United States Patent
Lee et al.

(10) Patent No.: US 6,562,614 B2
(45) Date of Patent: May 13, 2003

(54) ADP-RIBOSYLATION FACTOR-LIKE PROTEINS

(75) Inventors: Fang-Jen S. Lee, Taipei (TW); Chun-Fang Huang, Taipei (TW)

(73) Assignee: Yung Shin Pharmaceutical Ind. Co., Ltd., Tachia (TW)

( * ) Notice: Subject to any disclaimer, the term of this patent is extended or adjusted under 35 U.S.C. 154(b) by 35 days.

(21) Appl. No.: 09/848,813

(22) Filed: May 4, 2001

(65) Prior Publication Data

US 2002/0081713 A1 Jun. 27, 2002

Related U.S. Application Data

(63) Continuation of application No. 09/217,046, filed on Dec. 21, 1998, now abandoned.

(51) Int. Cl.[7] .............................. C12N 1/14; C12N 15/74
(52) U.S. Cl. ................................ 435/255.1; 435/255.2; 435/471
(58) Field of Search ........................... 435/255.1, 255.2, 435/471

(56) References Cited

PUBLICATIONS

Cavenagh et al. ADP–ribosylation factor (ARF)–like 3, a member of teh ARF family of GTP–binding progeins cloned from human and rat tissues. J. Biol. Chem. vol. 269(29): 18937–18942, 1994.*
Stearns et al. ADP ribosylation factor is an essential protein in Saccharomyces cerevisiae and is encoded by two genes. Mol. Cell. Biol. vol. 10(12):6690–6699, 1990.*
F.–J. Lee, C.–F. Huang, L.–M. Buu, and W.–L. Yu. "Characterization of a Novel Yeast ADP–Ribosylation Factor–Like Protein (yARL3)" Molecular Biology of the Cell, vol. 9, No. Suppl., Nov. 1998, p. 338A.
Database Swall 'Online! Accession No. P38116, Oct. 1, 1994. F.–J. Lee "ADP–ribosylation factor–like protein 1". Abstract.
Brown et al., "ADP–Ribosylation Factor, a Small GTP–Dependent Regulatory Protein, Stimulates Phospholipase D Activity", Cell 75:1137–1144, 1993.
Cavenagh et al., "ADP–ribosylation Factor (ARF)–like 3, a New Member of the ARF Family of GTP–binding Proteins Cloned from Human and Rat Tissues", The Journal of Biological Chemistry 269:18937–18942, 1994.
Cavenagh et al., "Intracellular Distribution of Arf Proteins in Mammalian Cells", The Journal of Biological Chemistry 271:21767–21774, 1996.
Clark et al., "Selective Amplification of Additional Members of the ADP–ribosylation Factor (ARF) Family: Cloning of Additional Human and Drosophila ARF–like genes", Proc. Natl. Acad. Sci. USA 90:8952–8956, 1993.
Cockcroft et al., "Phospholipase D: A Downstream Effector of ARF in Granulocytes", Science 263:523–526, 1994.

Donaldson et al., "ADP–ribosylation Factor, a Small GTP–binding Protein, is Required for Binding of the Coatomer Protein β–COP to Golgi Membranes", Proc. Natl. Acad. Sci. USA 89:6408–6412, 1992.
Houle et al., "ADP–ribosylation Factor Translocation Correlates with Potentiation of GTY γS–stimulated Phospholipase D Activity in . . . ", The Journal of Biological Chemistry 270:22795–22800, 1995.
Kahn et al., "Purification of a Protein Cofactor Required for ADP–ribosylation of the Stimulatory Regulatory Component of Adenylate Cyclase by Cholera Toxin", The Journal of Biological Chemistry 259:6228–6234, 1984.
Lee et al., "Characterization of an ADP–ribosylation Factor–like 1 Protein in Saccharomyces Cerevisiae", The Journal of Biological Chemistry 272:30998–31005, 1997.
Lee et al., "Characterization of Glucose–repressible ADP–ribosylation Factor 3 (ARF3) from Saccharomyces Cerevisiae", The Journal of Biological Chemistry 269:20931–20937, 1994.
Liscovitch et al., "Signal Transduction and Membrane Traffic: The ITP/Phosphoinositide Connection", Cell 81:659–662, 1995.
Palmer et al., "Binding of Coatomer to Golgi Membranes Requires ADP–ribosylation Factor", The Journal of Biological Chemistry 268:12083–12089, 1993.
Schurmann et al., "ARP is a Plasma Membrane–associated Ras–related GTPase with Remote Similarity to the Family of ADP–ribosylation Factors", The Journal of Biological Chemistry 270:30657–30663, 1995.
Schurmann et al., "Cloning of Two Novel ADP–ribosylation Factor–like Proteins and Characterization of Their Differential Expression in 3T3–L1 Cells", The Journal of Biological Chemistry 269:15683–15688, 1994.
Sewell et al., "Sequences of the Bovine and Yeast ADP–ribosylation Factor and Comparison to other GTP–Binding Proteins", Proc. Natl. Acad. Sci. USA 85:4620–4624, 1988.
Stamnes et al., "The Binding of AP–1 Clathrin Adaptor Particles to Golgi Membranes Requires ADP–Ribosylation Factor, a Small GTP–Binding Protein", Cell 73:999–1005, 1993.
Stearns et al., "ADP Ribosylation Factor is an Essential Protein in Saccharomyces Cerevisiae and is Encoded by Two Genes", Molecular and Cellular Biology 10:6690–6699, 1990.
Tamkun et al., "The Arflike Gene Encodes an Essential GTP–binding Protein in Drosophila", Proc. Natl. Acad. Sci. USA 88:3120–3124, 1991.
Traub et al., "Biochemical Dissection of AP–1 Recruitment onto Golgi Membranes", The Journal of Cell Biology 123:561–573, 1993.

(List continued on next page.)

*Primary Examiner*—Remy Yucel
*Assistant Examiner*—William Sandals
(74) *Attorney, Agent, or Firm*—Fish & Richardson P.C.

(57) ABSTRACT

The invention relates to a transgenic knockout yeast which has a disruption in the gene encoding for a yeast ADP-ribosylation factor-like protein.

10 Claims, No Drawings

OTHER PUBLICATIONS

Tsai et al., "Stimulation of Choleragen Enzymatic Activities by GTP and Two Soluble Proteins Purified from Bovine Brain", The Journal of Biological Chemistry 263:1768–1772, 1988

Tsai et al., "Effects of Brefeldin A and Accessory Proteins on Association of ADP–ribosylation Factors 1, 3, and 5 with Golgi", The Journal of Biological Chemistry 268:10820–10825, 1993.

Tsai et al., "Stimulation of Choleragen Enzymatic Activities by GTP and Two Soluble Proteins Purified from Bovine Brain", The Journal of Biological Chemistry 263:1768–1772, 1988

Whitney et al., "Cytoplasmic Coat Proteins Involved in Endosome Function", Cell 83:703–713, 1995.

Zeuzem et al., "Intravesicular Acidification Correlates with Binding of ADP–ribosylation Factor to Microsomal Membranes", Proc. Natl. Acad. Sci. USA 89:6619–6623, 1992.

Zhang et al., "Different ARF Domains Are Required for the Activation of Cholera Toxin and Phospholipase D", The Journal of biological Chemistry 270:21–24, 1995.

* cited by examiner

SEQUENCE LISTING

<160> NUMBER OF SEQ ID NOS: 9

<210> SEQ ID NO 1
<211> LENGTH: 610
<212> TYPE: DNA
<213> ORGANISM: Saccharomyces cerevisiae
<220> FEATURE:
<221> NAME/KEY: CDS
<222> LOCATION: (9)...(602)

<400> SEQUENCE: 1

-continued

```
ccgcacac atg ttt cat tta gtc aag gga ctt tac aat aat tgg aat aaa    50
        Met Phe His Leu Val Lys Gly Leu Tyr Asn Asn Trp Asn Lys
         1               5                  10 aag gaa caa tat tca att cta ata tta ggt cta gac aat gca ggc aaa    98
Lys Glu Gln Tyr Ser Ile Leu Ile Leu Gly Leu Asp Asn Ala Gly Lys
 15                  20                  25                  30 acg acg ttc ttg gag aca ttg aaa aag gaa tac tct ctg gcg ttc aaa   146
Thr Thr Phe Leu Glu Thr Leu Lys Lys Glu Tyr Ser Leu Ala Phe Lys
                 35                  40                  45 gcc ttg gaa aag ata cag cct acg gta gga caa aat gtg gcg aca ata   194
Ala Leu Glu Lys Ile Gln Pro Thr Val Gly Gln Asn Val Ala Thr Ile
             50                  55                  60 ccc gtt gac agt aaa cag atc ttg aag ttt tgg gat gta ggt ggt caa   242
Pro Val Asp Ser Lys Gln Ile Leu Lys Phe Trp Asp Val Gly Gly Gln
         65                  70                  75 gaa tca ctg aga tca atg tgg tcc gaa tac tat tcc cta tgt cat ggt   290
Glu Ser Leu Arg Ser Met Trp Ser Glu Tyr Tyr Ser Leu Cys His Gly
     80                  85                  90 ata att ttc att gtg gat agt tca gat aga gaa cga tta gac gaa tgt   338
Ile Ile Phe Ile Val Asp Ser Ser Asp Arg Glu Arg Leu Asp Glu Cys
 95                 100                 105                 110 tcc acg acc cta cag tca gtt gta atg gat gaa gaa att gaa ggt gta   386
Ser Thr Thr Leu Gln Ser Val Val Met Asp Glu Glu Ile Glu Gly Val
                115                 120                 125 ccc atc ttg atg ctg gcc aat aaa caa gat aga caa gat aga atg gaa   434
Pro Ile Leu Met Leu Ala Asn Lys Gln Asp Arg Gln Asp Arg Met Glu
            130                 135                 140 gta caa gat ata aaa gaa gta ttt aat aag att gcg gaa cat ata agc   482
Val Gln Asp Ile Lys Glu Val Phe Asn Lys Ile Ala Glu His Ile Ser
        145                 150                 155 gct aga gat agt agg gtt tta cca ata agc gca ttg act gga gaa ggt   530
Ala Arg Asp Ser Arg Val Leu Pro Ile Ser Ala Leu Thr Gly Glu Gly
    160                 165                 170 gtt aaa gac gct ata gaa tgg atg att gtt aga cta gaa agg aat aaa   578
Val Lys Asp Ala Ile Glu Trp Met Ile Val Arg Leu Glu Arg Asn Lys
175                 180                 185                 190 aag tca aga cca ccg att tat aaa tgataaag                          610
Lys Ser Arg Pro Pro Ile Tyr Lys
                195
```

<210> SEQ ID NO 2
<211> LENGTH: 198
<212> TYPE: PRT
<213> ORGANISM: Saccharomyces cerevisiae

<400> SEQUENCE: 2

```
Met Phe His Leu Val Lys Gly Leu Tyr Asn Asn Trp Asn Lys Lys Glu
 1               5                  10                  15

Gln Tyr Ser Ile Leu Ile Leu Gly Leu Asp Asn Ala Gly Lys Thr Thr
             20                  25                  30

Phe Leu Glu Thr Leu Lys Lys Glu Tyr Ser Leu Ala Phe Lys Ala Leu
         35                  40                  45

Glu Lys Ile Gln Pro Thr Val Gly Gln Asn Val Ala Thr Ile Pro Val
     50                  55                  60

Asp Ser Lys Gln Ile Leu Lys Phe Trp Asp Val Gly Gly Gln Glu Ser
 65                  70                  75                  80

Leu Arg Ser Met Trp Ser Glu Tyr Tyr Ser Leu Cys His Gly Ile Ile
                 85                  90                  95
```

```
Phe Ile Val Asp Ser Ser Asp Arg Glu Arg Leu Asp Glu Cys Ser Thr
            100                 105                 110

Thr Leu Gln Ser Val Val Met Asp Glu Glu Ile Glu Gly Val Pro Ile
        115                 120                 125

Leu Met Leu Ala Asn Lys Gln Asp Arg Gln Asp Arg Met Glu Val Gln
130                 135                 140

Asp Ile Lys Glu Val Phe Asn Lys Ile Ala Glu His Ile Ser Ala Arg
145                 150                 155                 160

Asp Ser Arg Val Leu Pro Ile Ser Ala Leu Thr Gly Glu Gly Val Lys
                165                 170                 175

Asp Ala Ile Glu Trp Met Ile Val Arg Leu Glu Arg Asn Lys Lys Ser
            180                 185                 190

Arg Pro Pro Ile Tyr Lys
        195
```

```
<210> SEQ ID NO 3
<211> LENGTH: 6
<212> TYPE: PRT
<213> ORGANISM: Saccharomyces cerevisiae
<220> FEATURE:
<221> NAME/KEY: VARIANT
<222> LOCATION: (1)...(6)
<223> OTHER INFORMATION: Xaa = Any Amino Acid

<400> SEQUENCE: 3

Trp Asp Val Gly Gly Gln
 1               5

<210> SEQ ID NO 4
<211> LENGTH: 4
<212> TYPE: PRT
<213> ORGANISM: Saccharomyces cerevisiae

<400> SEQUENCE: 4

Asn Lys Gln Asp
 1

<210> SEQ ID NO 5
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 5

Tyr Pro Tyr Asp Val Pro Asp Tyr Ala
 1               5

<210> SEQ ID NO 6
<211> LENGTH: 25
<212> TYPE: DNA
<213> ORGANISM: Artificial Sequence
<220> FEATURE:
<223> OTHER INFORMATION: primer for PCR

<400> SEQUENCE: 6
gcacatatgt tcatttagt caagg                                              25

<210> SEQ ID NO 7
<211> LENGTH: 28
<212> TYPE: DNA
<213> ORGANISM: Artificial Sequence
<220> FEATURE:
<223> OTHER INFORMATION: primer for PCR
```

<400> SEQUENCE: 7
ctcagtgatt ctagaccacc tacatccc                                           28

<210> SEQ ID NO 8
<211> LENGTH: 29
<212> TYPE: DNA
<213> ORGANISM: Artificial Sequence
<220> FEATURE:
<223> OTHER INFORMATION: primer for PCR

<400> SEQUENCE: 8
gatgtaggtg gtctagaatc actgagatc                                          29

<210> SEQ ID NO 9
<211> LENGTH: 31
<212> TYPE: DNA
<213> ORGANISM: Artificial Sequence
<220> FEATURE:
<223> OTHER INFORMATION: primer for PCR

<400> SEQUENCE: 9
ctttggatcc ttctttatca tttataaatc g                                       31

ADP-RIBOSYLATION FACTOR-LIKE PROTEINS

This application is a continuation, and claims the benefit of priority under 35 USC 120, of U.S. Application Ser. No. 09/217,046, filed Dec. 21, 1998 now abandoned. The disclosure of the prior application is considered part of, and is incorporated by reference in, the disclosure of this application.

BACKGROUND OF THE INVENTION

ADP-ribosylation factors (ARFs) are a family of proteins, each about 20 kDa in size and having the ability to bind and hydrolyze GTP. ARFs are also characterized by their ability to enhance the ADP-ribosyltransferase activity of cholera toxin (Kahn et al., J Biol Chem 259:6228–6234, 1984; and Tsai et al., J Biol Chem 263:1768–1772, 198). Some members of the ARF protein family are involved in regulating vesicle transport in cells as diverse as yeast and human cells.

The ARF-like protein (ARL) family is related to ARFs by amino acid sequence homology and, like ARFs, are characterized by their ability to bind and hydrolyze GTP. However, ARLs can be distinguished from ARFs as they do not enhance the ADP-ribosyltransferase activity of cholera toxin.

SUMMARY OF THE INVENTION

The invention features an antibody which specifically binds the ARL3 polypeptide having the amino acid sequence of SEQ ID NO:2, which can be encoded by a DNA molecule having the sequence of SEQ ID NO:1. By "specifically binds" is meant that the antibody binds the ARL3 polypeptide having the sequence of SEQ ID NO:2 but not specifically bind other molecules in that sample. For example, the antibody of the invention will not bind to other members of the yeast ARF and ARL families.

The invention also features a transgenic knockout yeast (e.g., *Saccharomyces cerevisiae*) having a homozygous disruption in its endogenous ARL3 gene, where the disruption prevents the expression of a functional ARL3 protein and the phenotype of the knockout yeast relative to a yeast having a wild type ARL3 gene includes impaired growth at about 15° C. The impaired growth can represent 50, 10, 5, or 1% of the growth of wild type yeast at that temperature. The disruption can include an insertion of a nucleic acid sequence into a wild type ARL3 gene in the genome of a parent yeast. Alternatively, the disruption can include an insertion into a mutated but functional ARL3 gene. In some embodiments, the nucleic acid sequence encodes a polypeptide (e.g., one that confers a selectable phenotype on the transgenic knockout yeast). For example, the parent yeast can be incapable of growth in a medium free of uracil, and the selectable phenotype can be the ability to grow in a medium free of uracil.

The antibody of the invention can be used to isolate and clone genes expressing polypeptides homologous to SEQ ID NO:2. Such an antibody is also useful for quantifying the amount of ARL3 in a sample. The transgenic knockout yeast of the invention is useful for identifying genes which are involved in vesicle transport. Such genes can be identified by their ability to complement the growth defect conferred by disruption of the ARL3 sequence.

Other features or advantages of the present invention will be apparent from the following drawings and detailed description, and also from the claims.

DETAILED DESCRIPTION

The invention relates to the identification of an expressed yeast ARL3 polypeptide and a nucleic acid which encodes it. The polypeptide and nucleic acid were then used to produce antibodies which specifically bind the ARL3 polypeptide and transgenic knockout yeast with a disruption in the ARL3 gene, respectively.

I. Antibodies

Both polyclonal and monoclonal anti-ARL3 antibodies are within the scope of the invention. Polyclonal anti-ARL3 antibodies can be prepared by immunizing a suitable animal, e.g., a rabbit, with an ARL3 immunogen. The anti-ARL3 antibody titer in the immunized animal can be monitored over time by standard techniques, such as with an enzyme linked immunosorbent assay (ELISA) using immobilized ARL3. The antibody molecules directed against ARL3 can be isolated from a mammal (e.g., from the blood of the mammal) and further purified by well-known techniques, such as protein A chromatography to obtain the IgG fraction. At an appropriate time after immunization, e.g., when the anti-ARL3 antibody titers are highest, antibody-producing cells can be obtained from the subject and used to prepare monoclonal antibodies by standard techniques, such as the hybridoma technique originally described by Kohler et al., Nature 256:495–497, 1975; Kozbor et al. (1983) Immunol Today 4:72, 1983; and Cole et al., Monoclonal Antibodies and Cancer Therapy, Alan R. Liss, Inc., pp. 77–96, 1985. The technology for producing various monoclonal antibody hybridomas is well known (see, e.g., Coligan et al. eds., Current Protocols in Immunology, John Wiley & Sons, Inc., New York, N.Y., 1994). Briefly, an immortal cell line (typically a myeloma) is fused to lymphocytes (typically splenocytes) from a mammal immunized with an ARL3 immunogen, and the culture supernatants of the resulting hybridoma cells are screened to identify a hybridoma producing a monoclonal antibody that binds ARL3.

Any of the many well known protocols used for fusing lymphocytes and immortalized cell lines can be applied for the purpose of generating an anti-ARL3 monoclonal antibody (see, e.g., Current Protocols in Immunology, supra; Galfre et al. (1977) Nature 266:55052; R. H. Kenneth, in Monoclonal Antibodies: A New Dimension In Biological Analyses, Plenum Publishing Corp., New York, N.Y. (1980); and Lerner (1981) Yale J. Biol. Med., 54:387–402. Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine (HAT medium). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol (PEG). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind ARL3, e.g., using a standard ELISA assay.

As an alternative to preparing monoclonal antibody-secreting hybridomas, a monoclonal anti-ARL3 antibody can be identified and isolated by screening a recombinant combinatorial immunoglobulin library (e.g., an antibody phage display library) with ARL3 to thereby isolate immunoglobulin library members that bind ARL3. Kits for generating and screening phage display libraries are commercially available (e.g., the Pharmacia Recombinant Phage Antibody System, Catalog No. 27-9400-01; and the Stratagene SurfZAPJ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al., Bio/Technology 9:1370–1372, 1991; Hay et al., Hum Antibod Hybridomas 3:81–85, 1992; Huse et al., Science 246:1275–1281, 1989; and Griffiths et al. EMBO J 12:725–734, 1993.

Additionally, recombinant anti-ARL3 antibodies, such as chimeric and humanized monoclonal antibodies, including both human and non-human portions, which can be made using standard recombinant DNA techniques, are also within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al., Science 240:1041–1043, 1988; Liu et al., Proc Natl Acad Sci USA 84:3439–3443, 1987; Liu et al., J Immunol 139:3521–3526, 1987; Sun et al., Proc Natl Acad Sci USA 84:214–218, 1987; Nishimura et al., Cancer Res 47:999–1005, 1987; Wood et al., Nature 314:446–449, 1985; Shaw et al., J Natl Cancer Inst 80:1553–1559, 1988; Morrison, Science 229:1202–1207, 1988; Oi et al., Bio/Techniques 4:214, 1986; U.S. Pat. No. 5,225,539; Jones et al., Nature 321:552–525, 1986; Verhoeyan et al., Science 239:1534, 1988; and Beidler et al., J Immunol 141:4053–4060, 1988.

II. Transgenic Yeasts

The first step in producing the transgenic yeast of this invention is to prepare a DNA sequence ("targeting molecule") that is capable of specifically disrupting an ARL3 gene in yeast cells carrying that gene and rendering that gene non-functional. The targeting molecule is then used to transfect yeast cells and to disrupt the functional ARL3 genes in those cells.

DNA targeting molecules that are capable, in accordance with this invention, of disrupting a functional ARL3 gene resident in cells may be produced using information and processes well known in the art.

A DNA targeting molecule of the present invention has two functions. Those functions are to integrate at a native resident ARL3 gene ("target gene locus") and to disrupt ARL3 gene expression associated with that locus so that no functional ARL3 expression is possible. Those two essential functions depend on two basic structural features of the targeting molecule.

The first basic structural feature of the targeting molecule is a pair of regions that are homologous to chosen regions of the target gene locus. That homology (in terms of both sequence identity and length) causes the targeting molecule to integrate by base pairing mechanisms ("homologous recombination") at the site chosen in the target gene locus in transfected cells.

Homologous recombination is the rearrangement of DNA segments at a sequence-specific site (or sites) within or between DNA molecules through base-pairing mechanisms. The present invention relates to a particular form of homologous recombination sometimes called "gene targeting". In gene targeting, an exogenous "targeting molecule" (or "targeting fragment") is introduced into cells. The targeting molecule has one or more regions of homology with a chromosomal gene to be modified or replaced ("target gene"). The regions of homology between the target gene and the targeting molecule result in site-specific integration of the exogenous sequence. Of course, the exogenous sequence may be designed to correct an existing defect in the resident gene or to disable ("disrupt") a functional resident gene. The present invention relates to disrupting ARL3 genes. Gene targeting, which affects the structure of a specific gene already in a cell, is to be distinguished from other forms of stable transformation wherein integration of foreign DNA for expression is not site-specific, and thus does not predictably affect the structure of any particular gene already in the cell.

The second basic structural feature of the targeting molecule of this invention is a disrupting sequence between the homologous regions. The disrupting sequence prevents expression of functional protein from the ARL3 target gene following the replacement of portion of that target gene by the integrated targeting molecule.

One of skill in the art will recognize that numerous embodiments of the ARL3 gene targeting molecule of the present invention may be constructed to fulfill the structural and functional requirements specified above. The example below describes the actual construction of an ARL3 gene targeting molecule used to produce the transgenic yeast of the present invention. The following discussion sets forth considerations and parameters that can be used to design other ARL3 gene targeting molecules.

Parameters of the targeting molecule that may be varied in the practice of the present invention include the lengths of the homologous regions, what regions of the target gene locus are to be duplicated as the homologous regions of the targeting molecule, the length of the disrupting sequence, the identity of the disrupting sequence, and what sequence of the target gene is to be replaced by the targeting molecule.

The length of the homologous regions that flank the disrupting sequence of the targeting molecules can vary considerably without significant effect on practice of the invention. The homologous flanking regions must be of sufficient length for effective heteroduplex formation between one strand of the targeting molecule and one strand of a transfected cell's chromosome, at the ARL3 target gene locus. Increasing the length of the homologous regions promotes heteroduplex formation and thus targeting efficiency. However, it will be appreciated that the incremental targeting efficiency accruing per additional homologous base pair eventually diminishes and is offset by practical difficulties in targeting molecule construction, as homologous regions exceed several thousand base pairs. An effect range for the length of each homologous region is 50 to 5,000 base pairs, with about 500 base pairs being desirable. It should be further noted that the precise length of the homologous regions in the DNA targeting molecule may depend in practice on the location of restriction sites in and around the ARL3 gene. For a discussion of the length of homology required for gene targeting, see Hasty et al., Mol Cell Biol 11:5586–91, 1991.

There is considerable latitude in choice of which regions of the target gene locus are duplicated as the homologous regions in the targeting molecule. The basic constraints are that the ARL3 target gene sequence to be replaced by the disrupting region must lie between the regions of the target gene locus duplicated as the homologous regions in the targeting molecule, and that replacement of the target gene sequence must render the ARL3 gene non-functional. It should be noted that the target gene locus nucleotide sequences chosen for homology in the targeting molecule remain unchanged after integration of the targeting molecule. Those sequences of the target gene locus are merely replaced by the duplicate (homologous) sequences in the targeting molecule. Identity between the chosen regions of the target gene locus and the homologous regions in the targeting molecule is the means by which the targeting molecule delivers the disrupting sequence precisely into the ARL3 target gene. The chosen regions of homology may lie within the ARL3 coding sequence, but it is not necessary that they do so. For example, in an embodiment of the present invention, one homologous region could be located 5' from the ARL3 gene, and the other homologous region could be located 3' from the ARL3 gene. The ARL3 initiation codon and 5' terminal region of the ARL3 coding sequence can lie between the chosen homologous regions and thus be replaced by the interrupting sequence, so that no portion of the protein can be expressed. When the interrupting sequence contains a selectable marker (or any other gene), there can be a termination codon downstream of the minimum required marker coding sequence, and in-frame with the marker coding sequence, to prevent translational read-through that might yield an ARL3 fusion protein with ARL3 activity. As a practical matter, other than the requirement that some critical site of the ARL3 gene lie between the homologous regions (so that it will be disrupted), the primary constraints on choice of homologous regions is the availability of the cloned sequences and the existence of restriction sites therein. Preferably, the regions chosen to be homologous regions will not include sequences longer than about 20 nucleotides that are known to occur elsewhere in the genome being modified. Extensive homology between the targeting molecule and other (non-target) sites in the genome might diminish targeting efficiency by diverting targeting molecules into non-productive heteroduplexes at non-target sites.

The length of the disrupting sequence separating the homologous regions in the targeting molecule can also vary considerably without significant effect on the practice of the present invention. The minimum length of the disrupting sequence is one base pair. Insertion of a single base pair in the ARL3 coding sequence would constitute a frame shift mutation and thus could prevent expression of a functional protein. Alternatively, a single base pair substitution could result in an amino acid substitution at a critical site in the protein and the expression of only non-functional protein. It should be recognized, however, that a single base pair alteration is susceptible to reversion to the wild type sequence through spontaneous mutation. For that reason, disrupting sequences longer than one base pair are sometimes more useful. At the other extreme, excessive length in the disrupting sequence would be unlikely to confer any advantage over a disrupting sequence of moderate length, and might diminish efficiency of transfection or targeting. Excessive length in this context is many times longer than the distance between the chosen homologous regions on the target gene. The length for the disrupting sequence can be from 2 to 2,000 base pairs. Alternatively, the length for the disrupting sequence is a length approximately equivalent to the distance between the regions of the target gene locus that match the homologous regions in the targeting molecule.

There is wide latitude in the choice of the disrupting sequence, since the disrupting function is not sequence-specific. It is necessary, however, that the nucleotide sequence of the disrupting region not express a functional ARL and not express a protein or polypeptide toxic to the transformed cell. The disrupting sequence should also not be extensively homologous to sites in the genome of the transfected cell. Such homology would be likely to diminish the efficiency of the targeting molecule, and might severely impair its function.

For some embodiments of the present invention it is preferred that the disrupting sequence have a dual function, i.e., be both a selectable marker and a disrupting sequence. In those embodiments, the length and identity of the disrupting sequence will be determined largely by the selectable marker coding sequence and associated expression control sequences. The selectable marker gene provides for positive selection of transfected cells that have taken up and integrated the targeting molecule. The need for a selectable marker will depend on the methods chosen for transfection of cells and transgenic yeast production. The choice of those methods, in turn, will depend on the species of yeast on which this invention is being practiced. Selectable markers include the antibiotic resistance gene, neomycin phosphotransferase ("neo"), or thymidine kinase, dihydrofolate reductase, hygromycin B phosphotransferase, xanthine-guanine phosphoribosyl transferase, adenosine deaminase, asparagine synthetase and CAD (carbamyl phosphate synthetase/aspartate transcarbamylase/dihydroorotase).

In this discussion, the targeting molecule is described as a linear DNA molecule. However, it should be recognized that a targeting molecule of the present invention could also be embodied as a circular DNA molecule. A circular targeting molecule can include a pair of homologous regions separated by a disrupting region, as described for a linear targeting molecule. Alternatively, a circular targeting molecule can include a single homologous region. Upon integration at the target gene locus, the circular molecule would become linearized, with a portion of the homologous region at each end. Thus, the single homologous region effectively becomes two homologous regions, as described in Watson et al., Molecular Biology of the Gene (4th Ed.), Benjamin/Cummings, Menlo Park, Calif., p. 606. One differing aspect of a circular targeting molecule with a single homologous region is that it inserts the disrupting sequence into the target gene and disrupts it without replacing any of the target gene. A second differing aspect is that the single homologous region must be within the target gene and located 5' to at least one critical site in the ARL3 coding sequence.

A transgenic yeast having a homozygous disruption in its ARL3 gene and exhibiting a observable phenotype due to the ARL3 disruption can be used to identify other genes which function in biochemical pathways affected by ARL3 protein. For example, an ARL3 knockout transgenic yeast exhibits a growth defect at 15° C. A library of DNA vectors which encode yeast polypeptides are then introduced into these knockout yeast. A transfected knockout yeast which exhibits wild-type growth at 15° C. can be inferred to contain a vector encoding a protein which complements the temperature-sensitive growth phenotype. Therefore, an analysis of the polypeptide encoded by that vector allows the identification of a gene or protein which is involved in vesicle transport.

Without further elaboration, it is believed that one skilled in the art can, based on the above disclosure and the isolation of ARL polypeptides and nucleic acids described below, utilize the present invention to its fullest extent. The following example is to be construed as merely illustrative of how one skilled in the art can isolate ARL polypeptides or nucleic acids from biological sources, and are not limitative of the remainder of the disclosure in any way. Any publications cited in this disclosure are hereby incorporated by reference.

EXAMPLE

Identification of Yeast ARL3. The yeast ARL3 (yARL3) gene was cloned by polymerase chain reaction using yeast DNA as template and primers complementary to sequences upstream or downstream of the Lpe21p gene (GenBank Accession No. U39205).

Conditions for PCR amplification were as follows: 35 cycles of 1 min at 95° C., 1 min at 52° C., and 1 min at 72° C.; followed by 72° C. for 10 min. The reaction was performed in 50 mM KCl, 10 mM Tris-Cl (pH 8.3), 1.5 mM $MgCl_2$, 0.01% gelatin, 20 mM of each dNTP, 0.1% Tween-20, 25 pmol of each amplification primer, and 2.5 units of Taq polymerase in a total volume 100 µl. Samples of reaction mixtures were subjected to electrophoresis in a 1.2% agarose gel. All PCR products were purified and subcloned. The ARL3 gene was sequenced by the dideoxy chain-termination method (Sanger et al., Proc Natl Acad Sci USA 74:5463–5467, 1977).

Sequencing of the yeast ARL3 gene revealed the following open reading frame: ccgcacacatgtttcatttagtcaagggactt-tacaataattggaataaaaaggaacaatattcaattctaatattaggtctagacaat-gcaggcaaaacgacgttcttggagacattgaaaaaggaatactctctggc-gttcaaagccttggaaaagatacagcctacg gtaggacaaaatgtggcga-caataccgttgacagtaaacagatcttgaagttttgggatgtaggtggtcaa-gaatcactgagat caatgtggtccgaatactattccctatgtcatgg-tataattttcattgtggatagttcagatagagaacgattagacgaatgttccacg-accctacagtcagttgtaatggatgaagaaattgaaggtgtacccatcttgatgc-tggccaataaacaagatagacaagatagaat ggaagtacaagatataaaagaag-tatttaataagattgcggaacatataagcgctagagatagtagggttttaccaataag-cgcat tgactggagaaggtgttaaagacgctatagaatggatgattgttagacta-gaaaggaataaaaagtcaagaccaccgatttataa atgataaag (SEQ ID NO:1).

This reading frame encodes the yeast ARL3 amino acid sequence: MFHLVKGLYNNWNKKEQYSILILGLD-NAGKTTFLETLKKEYSLAFKALEKIQPT VGQN-VATIPVDSKQILKF<u>WDVGGQ</u>ESLRSMWSEYYSLCHG-IIFIVDSSDRERLDE CSTTLQSVVMDEEIEGVPILMLA <u>NKQD</u>RQDRMEVQDIKEVFNKIAEHISARDSRV LPIS-ALTGEGVKDAIEWMIVRLERNKKSRPPIYK (SEQ ID NO:2).

As expected, the yeast ARL3 amino acid sequence contains the consensus GTP-binding sequences WDXGGQ (SEQ ID NO:3) and NKQD (SEQ ID NO:4), which are underlined in the above sequence.

Disruption of the ARL3 Gene in Yeast. To investigate the function of yARL3, we prepared strains of S. cerevisiae in which the ARL3 open reading frame was disrupted by a URA3 marker gene.

The S. cerevisiae strains were grown in yeast culture media prepared as described by Sherman et al., Methods in Yeast Genetics, Cold Spring Harbor Laboratory, Cold Spring Harbor, N.Y., 1986. YPD and YPGal contained 1% Bacto-yeast extract, 2% Bacto-peptone, and 2% glucose or 2% galactose, respectively; SD contained 0.7% Difco yeast nitrogen base (without amino acids) and 2% glucose. Nutrients essential for auxotrophic strains were supplied at concentrations specified in Sherman et al., supra. Sporulation, growth, and mating were carried out as described in Lee et al., J Bacteriol 171:5795–5802, 1989. Yeast were transformed by the lithium acetate method described in Ito et al., J Bacteriol 153:163–168, 1983.

yARL3DNA generated by PCR was subcloned into pGEM-7Zf plasmid resulting in pGyL3. The yeast URA3 gene was inserted at the single EcoNI site in the yARL3 gene as follows. The 3.8-kb DNA fragment containing the yeast URA3 gene and two hisG repeat sequences was excised from the plasmid pNKY51 (described in Alani et al., Genetics 116:541–545, 1987) by digestion with BglII and BamHI. The 5' overhangs were filled in with Klenow. Plasmid pGyL3 containing the yARL3 gene was linearized at the internal EcoNI site. The overhang ends were filled in with Klenow fragment and the cDNA was ligated to the 3.8-kb hisG-URA3-hisG fragment, resulting in pGyL3U.

Gene disruption mutants were constructed by a one-step gene replacement method (Rothstein, Methods Enzymol 101:202–211, 1983). Briefly, the 4.8-kb DNA fragment excised from pGyL3U, by digestion with XhoI and BamHI, was used to transform various Ura-strains, and uracil prototrophs were selected. DNA blot analysis of the URA+ cells confirmed that the yARL3 gene contained an additional 3.8-kb piece, corresponding to the hisG-URA3-hisG gene. Elimination of the URA3 and one hisG repeat was carried out as previously described in Lee et al., supra. Double deletions of yARL3 and yARL1 or yARL3 and yARF3 were performed in yeast arl3 mutants (arl3::hisG, ura3), arl1 mutants (arl1::hisG, ura3), and arf3 mutants (arf3::hisG, ura3).

A DNA fragment containing the yARL3::hisG-URA3-hisG sequence was used to transform ura3/ura3 diploid yeast (SEY6210.5; Ito et al., supra). Ura+ transformants were isolated and used to confirm the correct replacement of one of the two genomic copies of yARL3. The verified heterozygous diploids were then subjected to sporulation and tetrad dissection. On germination at 30° C., most diploid cells gave rise to four viable spores. Ura+ spores, but not ura–, contained the replacement of yARL3 and lacked yARL3 protein as determined by immunoprecipitation (procedure described below). Since each of the haploid strains containing the arl3 disruption was viable, yARL3 is not an essential gene under optimal growth conditions at 30° C. Total RNA from yeast (wild type or arl3 mutant) in mid-log growth in either glucose- or galactose-containing medium was subjected to electrophoresis; transferred to GeneScreen Plus; and hybridized with the yARL3 DNA probe, and after stripping, with a yeast β-tubulin probe. The 0.8-kb yARL3 RNA was not repressed by growth in glucose and was not detected in the arl3 mutant.

Cells with double deletions of yARL3 and yARF3, or yARL3 and yARL1 were viable. Proper disruption of the specific genes was confirmed by PCR on genomic DNA prepared from colonies of the mutants. This result confirmed that yARL3 is not essential for cell viability. In addition, it was found that the deletion was not complemented by yARL1 or yARF3.

To assess whether disruption of yARL3 can affect growth, growth rates of wild-type, arl3 mutant, and overexpressed yARL3 strains were determined. We constructed a recombinant yARL3 clone with a nine-amino acid influenza virus HA epitope (Wilson et al., Cell 37:767–778, 1984) fused to its C terminus. The HA-tagged allele (yARL3-HA) was under control of the ADH1 promoter, which drove expression in wild-type and arl3 mutant yeast.

The 3' end of the yARL3 cDNA was altered so that the encoded protein contained the HA epitope sequence YPY-DVPDYA (SEQ ID NO:5) at its C-terminus. The Q78L replacement was introduced using a two-step recombinant PCR technique. In the primary PCR reaction, overlapping 5'- and 3'-DNA fragments were generated. The 5'-oligonucleotide primer gcacatatgtttcatttagtcaagg (SEQ ID NO:6) and 5' Q78L oligonucleotide primer ctcagtgattctagaccacctacatccc (SEQ ID NO:7; point mutation is underlined) were used to amplify the 5' fragment. The 3'-fragment was generated using 3' Q78L oligonucleotide primer gatgtaggtggtctagaatcactgagatc (SEQ ID NO:8) in combination with the 3' end anti-sense oligonucleotide primer ctttggatccttctttatcatttataaatcg (SEQ ID NO:9). In the second fusogenic PCR reaction, the appropriate pairs of overlapping fragments were combined with the 5' and 3' end primers to generate the full-length Q78L mutant sequence. The full-length Q78L mutant DNA was then purified, subcloned, and the mutation confirmed by sequencing. The XhoI-XbaI fragment of yARL3-HA and yARL3 (Q78L) sequences were subcloned into the XhoI-XbaI sites in the pVT101U plasmid, an expression plasmid containing the ADH1 promoter (Vernet et al., Gene 52:225–233, 1987) to yield pVT101yL3HA and pVT101yL3(Q78L), respectively.

The arl3 mutants and yeast overexpressing yARL3 exhibited about 10% lower growth rates than wild-type yeast in glucose synthetic medium. A significant growth defect in yeast overexpressing wild-type yARL3 or yARL3 (Q78L) at 30° C. was not observed.

Growth of the various yeast mutants was also determined at different temperatures. Wild-type and arl3 mutant yeast cells were transformed with vectors harboring no insert (pVT101U), yARL3 (Q78L) insert, or wild-type yARL3. At 37° C. and 30° C., all yeast grew nearly as well as the wild-type strain. At 15° C., however, growth of the arl3 mutant was severely impaired. As expected, expression of yARL3 complemented the growth defect of the arl3 mutant, confirming that the growth defect of the null mutant was caused by disruption of yARL3. Moreover, overexpression of yARL3 (Q78L) in wild-type yeast caused a growth defect at 15° C. It was conceivable that overexpressed yARL3 (Q78L) interfered with yARL3-mediated vesicular transport at 15° C.

ARL Antibodies. To produce antibodies which specifically bind to yARL3, the yARL3 protein was recombinantly produced, isolated, and injected into rabbits as follows.

The open reading frame of yeast ARL3 was obtained by PCR, using primers that incorporated an unique NdeI site at the initiating methionine and an unique BamHI site six nucleotides after the stop codon. For the His-tag-yARL3 fusion protein, a DNA fragment containing the yARL3 coding region was generated by amplifying yeast genomic DNA with sequence-specific primers. The PCR product was purified and annealed to the expression vector pET15b (Novagen), yielding pET15byL3. For the nonfusion protein, PCR products were digested with NdeI and BamHI, purified, and annealed to expression vector pT7 (Haun et al., Gene 112:37–43, 1992), yielding pT7yARL3. BL21 (DE3) cells containing expression plasmids were grown to a density of $A_{600}=1.0$, at which time isopropyl-1-thio-β-D-galactopyranoside was added to a final concentration of 1 mM to induce expression. After three hours, cells were harvested by centrifugation, washed once in 20 mM Tris (pH 7.4) and 1 mM EDTA, and stored at −80° C. until needed. For large scale production of recombinant proteins, 5 ml of overnight culture were used to inoculate one liter of LB broth containing ampicillin (100 µg/ml). The cultures were grown at 37° C. with shaking. When the $A_{600}$ reached 0.6–0.8, protein production was induced with 0.5 mM isopropyl-1-thio-β-D-galactopyranoside for three hours, and bacteria were collected by centrifugation. Cell pellets were suspended in 10 ml of phosphate-buffered saline (pH 7.4) containing 0.5 mg/ml lysozyme and disrupted by sonication. The lysate was centrifuged after addition of Triton X-100 to 1% (v/v). The His-tagged fusion protein was isolated on $Ni^{2+}$-NTA resin (Qiagen, Chatsworth, Calif.) following the manufacturer's instructions. Purity was assessed by SDS-PAGE and staining with Coomassie blue. Protein was quantified by Coomassie blue or silver stain assays (BioRad).

Denatured purified proteins from SDS-PAGE gels were used as antigens to raise polyclonal antibodies in rabbits essentially as described in Harlow et al., Antibodies: A Laboratory Manual, Cold Spring Harbor Laboratory, Cold Spring Harbor, N.Y., 1988.

Rabbit sera were collected, cleared, and used for immunoblotting as follows. Whole cell extracts were prepared by harvesting three milliliters of a culture of $A_{600}$ units/ml. Cells were suspended in RIPA buffer (50 mM Tris-HCl [pH 8.0], 0.1% SDS, 0.5% deoxycholic acid, 150 mM NaCl, and 1% NP-40) to a final $A_{600}$ of 30. Whole-cell extracts were then prepared by vortexing with glass beads for 2 min at 4° C. and clarified by brief centrifugation. Proteins separated by SDS-PAGE were transferred electrophoretically to Immobilon-P membranes (Millipore Corp.). Incubation with antibodies was carried out in phosphate-buffered saline (pH 7.4) containing 0.1% Tween 20 and 5% dried skim milk at room temperature for 60 min. The anti-HA monoclonal antibody (HA. 11, Berkeley Antibody Co., Richmond, Calif.) and horseradish peroxidase-conjugated goat anti-mouse IgG+IgM (H+L) were each diluted 1:5000. Bound antibodies were detected with the ECL system (Amersham Corp.) following the manufacturer's instructions. Primary and secondary antibodies and luminol substrate were removed from the blot using the blot-stripping protocol (Amersham Corp.).

At a dilution of 1:5000, the polyclonal antibody specific for yARL3 did not cross-react with yARF1, yARF2, yARF3, or yARL1. In addition, the polyclonal antibody against yARF1, yARF2, yARF3, and yARL1 failed to react with yARL3 on Western blots. Immunoblotting with the yARL3 antiserum allowed detection of 1–2 ng of yARL3, whereas no signal was detected with recombinant yARF1, yARF2, yARF3, and yARL1 (up to 100 ng). Thus, the antibodies were specific for yARL3 and did not react with other members of the ARF or ARL families.

Endogenous Production of ARL. To confirm the presence of yARL3 protein in yeast, proteins from lysates of wild-type cells, arl3 mutants, and wild-type cells overexpressing yARL3 were separated by SDS-PAGE, and the gels stained with Coomassie Blue. Overexpressed yARL3 was detected by the antibody against yARL3.

As a more sensitive means to identify endogenous yARL3 protein, lysates were prepared from $^{35}S$-labelled cells. Yeast was grown at 30° C. overnight to an A600 of 0.5 in selective minimal medium containing 200 mM $(NH_4)_2SO_4$. After incubating for 10 min at 37° C. or 15° C., cells were transferred to sulfate-free, selective minimal medium (final $OD_{600}=5$), and incubated for 15 min at 37° C. or 30 min at 15° C. Then 30 µCi per $A_{600}$ unit of Pro-mix L-[$^{35}S$]-label (blend of $^{35}S$-methionine and $^{35}S$-cysteine, 14.3 mCi/ml) was added. After incubating 5 min at 37° C. or 20 min at 15° C., labeling was terminated by addition of 5% (v/v) of chase solution (0.3% cysteine (w/v), 0.4% methionine (w/v), and 100 mM $(NH_4)_2SO_4$). 1 ml samples were removed at the indicated time and added to equal volumes of ice-cold 20 mM $NaN_3$ in double-distilled $H_2O$. Cells were collected and washed with 10 mM $NaN_3$ in double-distilled $H_2O$. 300 µl glass beads and 300 µl of lysis buffer (50 mM Tris-Cl (pH 7.5), 1% SDS, 1 mM EDTA, and 1 mM PMSF) were added, and the mixture was agitated vigorously for 90 sec at room temperature before immersing in a boiling water bath for six min. Immunoprecipitation, electrophoresis, and autoradiography were performed essentially as described (Stirling et al., Mol Biol Cell 3:129–142, 1992), using anti-yARL3, anti-carboxypeptidase Y (CPY) or anti-alkaline phosphatase (ALP) antiserum.

Immunoprecipitation with yARL3 antibodies permitted detection of $^{35}$S-labeled endogenous yARL3 protein from wild-type and those overexpressing yARL3 (Q78L), but not arl3 mutant cells. These results demonstrated the existence of yARL3 in yeast at about 0.005% of total protein, an abundance less than that of yARF1 and yARF2, which represent approximately 0.03–0.1% of total yeast protein (Stearns et al., Mol Cell Biol 10:6690–6699, 1990).

ARL and Vesicular Transport. To evaluate the role of yARL3 in vesicular transport, both endocytotic and exocytotic pathways were examined. First, the glycosylation and proteolytic processing of carboxypeptidase Y (CPY) and vacuole alkaline phosphatase (ALP) was examined. CPY and ALP are enzymes which are transported from the endoplasmic reticulum (ER) to the Golgi to vacuoles by distinct sorting machineries (Cowles et al., EMBO J 16:2769–2782, 1997). Cells were pulse-chased with $^{35}$S-labeled cysteine and methionine at the permissive temperature (37° C.) or non-permissive temperature (15° C.). CPY and ALP were then immunoprecipitated.

The core-glycosylated P1 form of the CPY proenzyme in the ER is converted to the P2 form by further glycosylation in the Golgi apparatus and finally is proteolytically processed in the vacuole to the mature form. ALP is a type II membrane protein that is delivered to the vacuole in proenzyme form. The sorting of ALP from late Golgi to the vacuole is reported to differ from that of CPY (Cowles et al., supra). Upon arrival at the vacuole, the precursor ALP is cleaved at a site near the carboxy-terminus to yield a mature membrane-spanning form of the protein.

At the permissive temperature, similar to the wild-type cells, the arl3 mutant yeast readily converted CPY and ALP from the ER to Golgi and vacuole forms. The arf1 mutant, however, accumulated core-glycosylated CPY in the P1 form and pro-ALP form as expected. At the non-permissive temperature, processing of alkaline phosphatase in the arl3 mutant was delayed, whereas processing of carboxypeptidase Y was minimally affected. Thus, yARL3 may have a biological function different from that of yARF1/yARF2 and may be involved in a distinct ER to Golgi or Golgi to vacuole protein transport pathway.

To determine whether yARL3 might function in an endocytic pathway, we investigated the effect of yARL3 on the uptake of the fluid-phase marker, Lucifer Yellow (LY). LY is a small fluorescent organic anion that is often used as a marker for fluid-phase endocytosis. The uptake of LY is time and energy dependent and requires certain proteins that are important for endocytosis.

Endocytosis of Lucifer Yellow CH was performed as described in Dukic et al., Methods Enzymol 194:697–710, 1991. Briefly, one ml of $A_{600}$ unit/ml of mid-log phase cells was collected, suspended in 90 μl of fresh medium, and added to 10 μl of Lucifer Yellow CH (40 mg/ml). Cells were incubated at 30° C. for 30 to 90 min or at 15° C. for 2 to 4 hours, harvested, washed three times in endocytosis wash buffer (50 mM succinate and 2 mM $NaN_3$ [pH 5.0]), and suspended in 10 μl of the same buffer. 2.5 μl samples of cells were mixed with equal volume of 1.6% liquid solution of low-melting point agarose at 45° C. and mounted on microscope slides for visualization by fluorescence microscopy using FITC optics.

Wild-type and arl3 mutant cells were incubated with LY at either the permissive temperature (30° C.) or non-permissive temperature (15° C.) for various times. Cells were washed, mounted, and viewed under phase-contrast and fluorescence optics. At permissive temperature, arl3 mutant cells appeared defective in accumulation of LY after incubation for 30 min, but not after 90 min. Vacuolar morphology of both wild type and arl3 mutants appeared normal. At the non-permissive temperature, fluid-phase endocytosis of LY was found to be impaired in arl3 mutant compared to wild type cells after incubation for 2 hours. After incubation with LY for 4 hours at the non-permissive temperature, wild-type cells exhibited unambiguous vacuolar staining, whereas most of the arl3 cells exhibited less clearly stained vacuoles. Moreover, arl3 mutants were found to contain vacuoles of aberrant sizes after incubation at non-permissive temperature for 4 hours.

Subcellular Localization of ARL. The cellular localization of yARL3 was determined as follows. Cells were harvested by centrifugation from 50 ml cultures and grown in YPD to mid-exponential phase ($A_{600}=1$). Cells (0.5 g) were washed by repeated suspension in ice-cold $NaN_3$ (10 mM in double-distilled $H_2O$) followed by centrifugation. The cells were then incubated with Lyticase to form spheroplasts and suspended in 0.2 ml of ice-cold lysis buffer (20 mM triethanolamine (pH 7.2), 1 mM EDTA, and 0.8 M sorbitol) containing protease inhibitors (aprotinin, leupeptin, and pepstatin, each at 1 μg/ml; 1 mM benzamidine; and 1 mM PMSF). The cells were disrupted on ice with 20 strokes in a Dounce homogenizer. The cell lysate was centrifuged (450 g) twice for 10 min to remove unbroken cells and cellular debris. For gradient fractionation of cell organelles, 0.8 ml of the clarified supernatant was loaded on top of a manually generated five-step sucrose gradient (0.8 ml each of 60, 50, 40, 30, 20% sucrose in lysis buffer), which was then subjected to centrifugation in a Beckman SW55 rotor (170,000×g) for 3.5 h at 4° C. Twelve fractions were collected manually from the top. Proteins in samples (100 μl) of fractions were precipitated with 10% TCA, separated by SDS-PAGE, and analyzed by immunoblotting.

The presence of yARL3, yARF1, Emp47p (Golgi marker protein; described in Schroder et al., J Cell Biol 131:895–912, 1995), and ALP (vacuole marker protein) in various fractions was assessed by Western blot analysis. Most of the yARL3 was at the top of the gradient, representing an apparent soluble cytoplasmic form.

Since yARL3 appeared to dissociate from membranes upon cell lysis, the intracellular localization of yARL3 was determined by indirect immunofluorescence.

Cells were grown in 5 ml of minimal selective medium with 2% glucose to a density of $1-2\times10^7$ cells/ml and prepared for indirect immunofluorescence as described in Schroder et al, supra, with the following modifications: 0.6 ml of 37% formaldehyde were added to each culture for fixation, and the cultures were gently shaken at 30° C. for 2 hours. Cells were collected by centrifugation (2,500×g, 5 min), washed once in 5 ml of 0.1 M potassium phosphate (pH 6.5) buffer, suspended in 1 ml of solution P (1.2 M sorbitol, 0.1 M potassium phosphate, pH 6.5), and incubated at 30° C. for 30 min with 5 to 10 μl of Lyticase (10,000 u/ml in solution P) containing 1% β-mercaptoethanol. The cells were collected by centrifugation (3,000×g, 5 min), washed with solution P, and suspended in 100–200 μl of solution P. Samples (30 μl) of cells were placed in each well of a multiwell slide that had been coated with 0.1% polylysine. Following aspiration of non-adherent excess cells, the slides were washed once with a washing buffer containing 100 mM Tris-HCl (pH 9.0) and 150 mM NaCl, then incubated for 1 hour with antibody blocking buffer (100 mM Tris-HCl (pH 9.0), 150 mM NaCl, 5% non-fat milk, 0.1% Tween 20). This incubation was followed by a 2 hour incubation with the primary antibody in antibody blocking buffer. The slides were then washed twice with the washing buffer. After 2 hours of incubation with the secondary antibody, cells were washed extensively with the washing buffer again. Mouse monoclonal anti-HA antibody 12CA5, and fluorescein isothiocyanate (FITC)-conjugated secondary antibodies (Cappel) were diluted 1:1000 and 1:300, respectively, before use. Texas Red-conjugated goat anti-rabbit IgG antibody (Amersham Corp.) was used as the detection antibody.

Nuclei were visualized by staining with H33258 (2 μg/ml), which was included in mounting solution. Polyclonal anti-Kar2 antibody was kindly provided by Dr. Mark Rose. Fluorescence microscopy was performed with a Nikon Microphot SA microscope. Cells were viewed at 1000×.

When yARL3-HA was over-expressed in wild-type cells, most of the immunoreactive yARL3 appeared concentrated in a continuous circum-nuclear distribution typical of ER staining. In parallel experiments, we observed similar staining patterns with both antibody 12CA5 directed against the HA-epitope of yARL3-HA, and anti-Kar2p (Rose et al., Cell 57, 1211–1221, 1989). In both cases, neither punctate staining typical for Golgi localization nor staining of the vacuole was evident. Because yARL3 was overexpressed using a muticopy-plasmid, large variations from cell to cell in levels of HA-yARL3 expression were seen, and more cytosolic yARL3 was detected as diffuse than as reticular staining. From the combined results of subcellular fractionation and indirect immunofluorescence, it appears that yARL3 was probably associated in part with ER membranes.

Biochemical Properties of ARL. To determine whether the yARL3 gene product has ARF activity, recombinant yARL3 synthesized in and purified from *E. coli* was assayed as follows.

Purified His-tagged yARL3 or yARF1 fusion protein were tested for their ability to stimulate cholera toxin-catalyzed auto-ADP-ribosylation. 5 μg of protein was added to 100 μl reaction mixtures containing 50 mM potassium phosphate (pH 7.5), 5 mM $MgCl_2$, 20 mM thymidine, 0.1 mM GTP, 0.003% SDS, 10 μM [$^{32}$P]NAD (2 mCi), and 1 μg of activated CTA. After incubation at 30° C. for 1 hour, reactions were terminated by the addition of 1.0 ml of ice-cold 7.5% trichoroacetic acid. After precipitation overnight at 4° C. and centrifugation, the protein was dissolved in 60 mM Tris (pH 6.8), 10% glycerol, 5% 2-mercaptoethanol, 3% SDS, and 0.006% bromophenol blue by placing the mixture in a 65° C. water bath for 10 min. The proteins was separated by SDS-PAGE in 12% gels, and transferred to nitrocellulose membranes, which were exposed to X-ray film for 24 hours.

Binding of GTP to purified recombinant yARL3 was determined by the filter trapping method described in Northup et al., J Biol Chem 258:11361–11368, 1983. 1 μg of His-tagged yARL3 fusion protein was incubated at 30° C. in 20 mM HEPES (pH 7.5), 100 mM NaCl, 1 mM dithiothreitol, 1 mM EDTA, 0.5 mM $MgCl_2$, 20 μg/ml bovine serum albumin (BSA), and 10 μM [γ-$^{35}$S]GTP (Amersham, >1000 Ci/mmol) in a final volume of 50 μl. The reaction optionally included 3 mM D,L-α-dimyristoylphosphatidylcholine (DMPC) and 2.5 mM (0.1%) sodium cholate. Duplicate or triplicate samples were transferred to 2 ml of ice-cold 20 mM Tris-Cl (pH 7.4), 100 mM NaCl, 10 mM $MgCl_2$, and 1 mM dithiothreitol before rapid filtration on a 0.45 μm HA filters (Millipore, Bedford). The amount of nucleotide bound to the fusion protein was quantified by scintillation counting. Data were fitted to a first-order rate equation.

GTP hydrolysis was determined by binding [α-$^{32}$P] GTP to 5.0 μM recombinant yARL3 protein, as described by Randazzo et al. (J Biol Chem 269:10758–10763, 1994), followed by dilution (1:9) into 25 mM HEPES (pH 7.4), 100 mM NaCl, 2.5 mM $MgCl_2$, 0.1% Triton X-100, 1 mM dithiothreitol, 1 mM GTP with bovine brain phosphoinositides (1 mg/ml), and incubation at 30° C. Every 5 min, samples were transferred to 2 ml of ice-cold 20 mM Tris-Cl (pH 7.4), 100 mM NaCl, 10 mM $MgCl_2$, and 1 mM dithiothreitol. The conversion of GTP to GDP was determined by thin-layer chromatography as described in Northup et al., supra. A blank without protein was used to determine background, which was subtracted from samples containing protein.

The His-tagged yARL3 fusion protein did not stimulate auto-ADP-ribosylation of cholera toxin A1 protein, in the presence of 100 μM GTP and SDS. GTP binding to yARL3 was concentration-dependent and was maximal after incubation for 60 min at 30EC. With DMPC/cholate, recombinant yARL3 bound 3.2"0.3 pmol of GTP/μg protein. Without DMPC/cholate, yARL3 bound 1.5"0.2 pmol of GTP/μg protein. Therefore, GTP binding to yARL3 was modified by the added phospholipid/detergent.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

What is claimed is:

1. A transgenic knockout yeast comprising a homozygous disruption in its endogenous ARL3 gene, wherein the disruption prevents the expression of a functional ARL3 protein, and the knockout yeast is impaired for growth at about 15° C. relative to a yeast having a wild type ARL3 gene.

2. The transgenic knockout yeast of claim 1, wherein the transgenic knockout yeast is a *Saccharomyces cerevisiae*.

3. The transgenic knockout yeast of claim 2, wherein the disruption includes an insertion of a nucleic acid sequence into a wild type ARL3 gene in the genome of a parent yeast.

4. The transgenic knockout yeast of claim 3, wherein the nucleic acid sequence encodes a polypeptide.

5. The transgenic knockout yeast of claim 4, wherein expression of the polypeptide confers a selectable phenotype on the transgenic knockout yeast.

6. The transgenic knockout yeast of claim 5, wherein the parent yeast is incapable of growth in a medium free of uracil, and the selectable phenotype is the ability to grow in a medium free of uracil.

7. The transgenic knockout yeast of claim 1, wherein the disruption includes an insertion of a nucleic acid sequence into a wild type ARL3 gene in the genome of a parent yeast.

8. The transgenic knockout yeast of claim 7, wherein the nucleic acid sequence encodes a polypeptide.

9. The transgenic knockout yeast of claim 8, wherein expression of the polypeptide confers a selectable phenotype on the transgenic knockout yeast.

10. The transgenic knockout yeast of claim 9, wherein the parent yeast is incapable of growth in a medium free of uracil, and the selectable phenotype is the ability to grow in a medium free of uracil.

* * * * *